(12) United States Patent
Kasahara et al.

(10) Patent No.: US 6,806,080 B2
(45) Date of Patent: Oct. 19, 2004

(54) HYBRID VECTORS FOR GENE THERAPY

(75) Inventors: Noriyuki Kasahara, Los Angeles, CA (US); Collin Higo, Reno, NV (US); Harris Soifer, West Hills, CA (US); Kohnosuke Mitani, Los Angeles, CA (US)

(73) Assignees: University of Southern California, Los Angeles, CA (US); The Regent of the University of California, Oakland, CA (US)

( * ) Notice: Subject to any disclaimer, the term of this patent is extended or adjusted under 35 U.S.C. 154(b) by 0 days.

(21) Appl. No.: 10/102,610

(22) Filed: Mar. 19, 2002

(65) Prior Publication Data

US 2003/0017597 A1 Jan. 23, 2003

Related U.S. Application Data

(62) Division of application No. 09/484,901, filed on Jan. 18, 2000, now Pat. No. 6,576,463.
(60) Provisional application No. 60/116,150, filed on Jan. 16, 1999.

(51) Int. Cl.$^7$ .................. C12N 15/861; C12N 15/867; C12N 15/63; C07H 21/04
(52) U.S. Cl. .................. 435/320.1; 435/69.1; 435/455; 435/456; 435/457; 435/325; 536/23.1; 536/23.72; 536/24.1
(58) Field of Search .......................... 435/320.1, 69.1, 435/455, 456, 457, 325; 536/23.1, 23.72, 24.1

(56) References Cited

U.S. PATENT DOCUMENTS

| 5,591,624 A | 1/1997 | Barber et al. |
| 6,156,497 A | 12/2000 | Kaleko |

FOREIGN PATENT DOCUMENTS

| WO | WO 97/15679 | * 5/1997 |

OTHER PUBLICATIONS

Bilbao, G., Feng, M., Rancourt, C., Jackson, W.H., Curiel, D.T., (Jul. 1997) Adenoviral/Retroviral Vector Chimeras: A Novel Strategy to Achieve High–Efficiency Stable Transduction In Vivo, The FASEB Journal, vol. 11, 624–634.
Boeck, J., (1997) LINEs and Alus–the polyA connection, Nature Genetics 16, 6–7.
Cannon P. M. et al., (1996), Murine leukemia virus–based Tat inducible LTR replacement vectors: a new system for anti–HIV gene therapy. J. Virol. 70, 8234–40.
Chakraborty, A. K. et al., (1994) Transmission of endogenous VL30 retrotransposons by helper cells used in gene therapy, Cancer Gene Ther. 1, 113–8.

Clemens, P. R. et al., (1996) In vivo muscle gene transfer of full–length dystrophin with an adenoviral vector that lacks all viral genes, Gene Ther. 3, 965–72.
Englehardt, J. F. et al. (1993). Direct gene transfer of human CFTR into human bronchial epithelia of xenografts with E1–deleted adenoviruses. Nat.Genet. 4, 27–34.
Feng, Q. et al. (1996). Human L1 retrotransposon encodes a conserved endonuclease required for retrotranposition. Cell 87, 905–16.
Fisher, K. J. et al. (1996). A novel adenovirus–adeno–associated virus hybrid vector that displays efficient rescue and delivery of the AAV genome. Hum. Gene Ther. 7, 2079–87.
Flotte, T. R. et al. (1993). Stable in vivo expression of the cystic fibrosis transmembrane conductance regulator with an adeno–associated virus vector. Proc. Natl. Acad. Sci. USA 90, 10613–7.
Flotte, T. R. et al. (1994) Adeno–associated virus vector gene expression occurs in nondividing cells in the absence of vector DNA integration. Am J Respir Cell. Mol. Biol. 11, 517–21.
Gao, G. P. et al. (1996). Biology of adenovirus vectors with E1 and E4 deletions for liver–directed gene therapy. J. Virol. 70, 8934–43.
Gueiros–Filho, F. J. and Beverly, S. M. (1997) Trans–kingdom transposition of the Drosophila element Mariner within the protozoan Leishmania. Science, 276: 1716–1719.
Haecker, S. E. et al.(1996). In vivo expression of full–length human dystrophin from adenoviral vectors deleted of all viral genes. Hum. Gen Ther. 7, 1907–14.
Halbert, C. L. et al. (1995). Adeno–associated virus vectors transduce primary cells much less efficiently than immortalized cells. J. Virol. 69, 1473–9.
Hattori, M. et al. (1986). L1 family of repetitive DNA sequences in primates may be derived from a sequence encoding a reverse transcriptase–related protein. Nature 321, 625–628.
Hodgson, C.P., Xu, G., Solaiman, F., Zink, M.A., (1997) Biosynthetic Retrovectoring Systems for Gene Therapy, Journal of Molecular Medicine, 75:249–258.
Hohjoh, H., and Singer, M. F. (1996). Cytoplasmic ribonucleoprotein complexes containing human LINE–1 protein and RNA. EMBO J. 15, 630–639.

(List continued on next page.)

*Primary Examiner*—David Guzo
(74) *Attorney, Agent, or Firm*—Bingham McCutchen LLP

(57) ABSTRACT

The invention discloses hybrid vectors for delivering genes or other nucleic acids into mammalian cells. The hybrid vectors of the invention contain both a helper dependent adenoviral portion and a second portion derived from a transposon. Such vectors provide efficient transduction of quiescent cells and provide for stable integration of the gene to be delivered.

14 Claims, 6 Drawing Sheets

OTHER PUBLICATIONS

Holmes, S. E., Singer, M. F., and Swergold, G. D. (1992). Studies on p40, the leucine zipper motif–containing protein encoded by the first open reading frame of an active human LINE–1 transposable element. J. Biol. Chem. 267, 19765–19768.

Hwang, L. H. S., and Gilboa, E. (1984). Expression of genes introduced into cells by retroviral infection is more efficient than that of genes introduced into cells by DNA transfection. J. Virol. 50, 417–424.

Ivics, Z. et al. (1997). Molecular reconstruction of Sleeping Beauty, a Tc1–like transposon from fish, and its transposition in human cells. Cell 91,501–10.

Johnston, K.M., Jacoby, D., Pechan, P.A., Fraefel, C., Borghesani, P., Schuback, D., Dunn, R.J., Smith, F.I., Breakefield, X.O., (Feb. 10, 1997) HSC/AAV Hybrid Amplicon Vectors Extend Transgene Expression in Human Glioma Cells, Human Gene Therapy, 8:359–370.

Kaplan, J. M. et al. (1997). Characterization of factors involved in modulating persistence of transgene expression from recombinant adenovirus in the mouse lung. Hum. Gene Ther. 8, 45–56.

Kingsman, A.J., Burns. N.R., Layton, G.T., Adams. S.E., (1995) Yeast Retrotransposon Particles as Antigen Delivery Systems, Annals of the New York Academy of Sciences, vol. 754, 1–404, pp. 202–213.

Kochanek, S. et al. (1996). A new adenoviral vector: Replacement of all viral coding sequences with 28 kb of DNA independently expressing both full–length dystrophin and beta–galactosidase. Proc. Natl. Acad. Sci. USA 93, 5731–6.

Lieber, A. et al. (1996). Recombinant adenoviruses with large deletions generated by Cre–mediated excision exhibit different biological properties compared with first–generation vectors in vitro and in vivo. J. Virol. 70, 8944–60.

Lucher, L. (1995). Abortive adenovirus infection and host range determinants. In The Molecular Repertoire of Adenoviruses, W. Doerfler and P. Bohm, eds. (Berlin, Heidelberg, New York: Springer), pp. 119–152.

Mann, R. et al. (1983). Construction of a retrovirus packaging mutant and its use to produce helper–free defective retrovirus. Cell 33, 153–159.

Markowitz, D. et al. (1988). A safe packaging line for gene transfer: Separating viral genes on two different plasmids. J. Virol. 62, 1120–1124.

Miller, A. D., and Buttimore, C. (1986). Redesign of retrovirus packaging cell lines to avoid recombination leading to helper virus production. Mol. Cell. Biol. 6, 2895–2902.

Minakami, R. et al. (1992). Identification of an internal cis–element essential for the human L1 transcription and a nuclear factor(s) binding to the element. Nucl. Acids Res. 12, 3139–3145.

Mitani, K. et al. (1995A). Rescue, propagation, and partial purification of a helper virus–dependent adenovirus vector. Proc Natl Acad Sci U S A 92, 3854–8.

Mitani, K. et al. (1995B). Gene targeting in mouse embryonic stem cells with an adenoviral vector. Somat. Cell. Mol. Genet. 21, 221–231.

Moran, J. V. et al. (1996). High frequency retrotransposition in cultured mammalian cells. Cell 87, 917–27.

Mulligan, R. (1993). The basic science of gene therapy. Science 260, 926–932.

Parks, R. J. et al. (1996). A helper–dependent adenovirus vector system: removal of helper virus by Cre–mediated excision of the viral packaging signal. Proc. Natl. Acad. Sci. USA 93, 13565–70.

Parks, R. J., and Graham. F. L. (1997). A helper–dependent system for adenovirus vector production helps define a lower limit for efficient DNA packaging, J. Virol. 71, 3293–8.

Plasterk, R. H. (1996) The Tc1/mariner transposon family. Curr. Top. Microbiol. Immunol. 204, 125–43.

Plasterk, R.H. (1999) Resident aliens: the Tc1/mariner superfamily of transposable elements. Trends Genet. 15, 326–32.

Roessler, B. J. et al. (1995). Inhibition of interleukin–1–induced effects in synoviocytes transduced with the human IL–1 receptor antagonist cDNA using an adenoviral vector. Hum. Gene Ther. 6, 307–316.

Sassaman, D.M. et al.(1997). Many human L1 elements are capable of retrotransposition. Nat. Genet. 16, 37–43.

Savard, N., Cossett, F.L., Epstein, A.L., (May 1997) Defective Herpes Simplex Virus Type 1 Vectors Harboring gag, pol, and env Genes Can Be Used to Rescue Defective Retrovirus Vectors, Journal of Virology, 71(5), 4111–4117.

Scott, A. F. et al. (1987). Origin of the human L1 elements: proposed progenitor genes deduced from a consensus DNA sequence. Genomics 1, 113–125.

Singer, M. F. et al. (1993). LINE–1: a human transposable element. Gene 135, 183–188.

Soneoka, Y. et al. (1995). A transient three–plasmid expression system for the production of high titre retroviral vectors. Nucl. Acid Res. 23, 628–633.

Swergold, G. D. (1990). Identification, characterization, and cell specificity of a human LINE–1 promoter. Mol. Cell. Biol. 10, 6718–6729.

Thrasher, A. J., de Alwis, M., Casimir, C. M., Kinnon, C., Page, K., Lebkowski, J., Segal, A. W., and Levinsky, R. J. (1995). Generation of recombinant adeno–associated virus (rAAV) from an adenoviral vector and functional reconstitution of the NADPH–oxidase. Gene Ther. 2, 481–5.

Torrent, C. et al. (1994). Analytical study of rat retrotransposon VL30 RNA dimerization in vitro and packaging in murine leukemia virus. J. Mol. Biol. 240, 434–44.

Varmus, H. (1988). Retroviruses. Science 240, 1427–1435.

Weiss, R. et al. (1984). RNA Tumor Viruses: Molecular Biology of Tumor Viruses (Cold Spring Harbor, N.Y.: Cold Spring Harbor Laboratory) (Only front page and table of contents submitted).

Xiong, Y., and Eickbush, T. H. (1990). Origin and evolution of retroelements based upon their reverse transcriptase sequences. EMBO J. 9, 3353–3362.

Yang, Y. et al. (1995). Cellular and humoral immune responses to viral antigens create barriers to lung–directed gene therapy with recombinant adenoviruses. J. Virol. 69, 2004–15.

Yoshida, Y., Emi, N., Hamada, H., (1997) VSV–G–Pseudotyped Retroviral Packaging through Adenovirus–Mediated Inducible Gene Expression, Biochemical and Biophysical Research Communications, 232, 379–382.

Yoshimoto, T. et al. (1993). Identification of amino acid residues critical for infection with ecotropic murine leukemia retrovirus. J. Virol. 67, 1310–1314.

Yant, S.R., et al., "Transposition from a gutless adeno–transposon vector stabilizes transgene expression in vivo" (2002) Nature Biotechnology vol. 20, pp. 999–1005.

\* cited by examiner

AdLC8cluc

HYBRID VECTORS FOR GENE THERAPY

CROSS REFERENCE TO RELATED APPLICATION

This application is a divisional of U.S. patent application Ser. No. 09/484,901 filed Jan. 18, 2000 now U.S. Pat. No. 6,576,463, which claims the benefit of provisional application Ser. No. 60/116,150 filed Jan. 16, 1999, the disclosure of which is incorporated by reference in its entirety.

GOVERNMENT SUPPORT

The government may have certain rights in this invention pursuant to grant no. 1R21DK054280-01 from the National Institutes of Health.

FIELD OF THE INVENTION

The invention relates to the field of medicine and in particular to vectors for delivery of nucleic acids into cells and to vectors useful for gene therapy.

BACKGROUND

One of the foremost obstacles to the practical implementation of human gene therapy is the lack of an optimal method for the direct delivery of therapeutic genes to quiescent tissues in vivo. A number of vector systems based on viral components have been developed; however, of these individual virus vector systems, none is optimal and each system displays significant drawbacks.

Retroviruses as vehicles for the delivery of genes into eukaryotic cells have several advantages (Hwang and Gilboa, 1984; Varmus, 1988): 1) gene transfer is relatively efficient; 2) stable integration into the host cell DNA is a natural part of the retroviral life cycle, and therefore the integrated provirus is passed on to all daughter cells, and continues to direct the nonlytic production of its encoded products; and 3) replication-defective vectors can be created by deletion of essential viral genes, which renders the vectors incapable of secondary infection (Mann et al., 1983; Markowitz et al., 1988; Miller and Buttimore, 1986). In spite of these advantages, retroviral gene transfer in its current form has several drawbacks. Most retroviral vectors in current use are traditionally based on Moloney murine leukemia virus (MLV), which requires cell division during infection so that the nucleocapsid complex can gain access to the host cell genome, and hence cannot infect non-dividing cells (Mulligan, 1993; Varmus, 1988). Many cell types are considered to be largely quiescent in vivo, and furthermore, most retroviral vectors are produced from packaging cells at titers on the order of only $10^{6-7}$ colony-forming units (cfu) per ml, which is barely adequate for transduction in vivo. Therefore, retroviral gene transfer in vivo is inefficient, and the traditional approach which has been adopted for retroviral vectors has been to transduce primary cells in culture by the ex vivo method, followed by re-implantation of the transduced cells. This approach requires surgical acquisition, isolation, and culture of autologous cells, and thus is labor-intensive and invasive, and limits the scope of ex vivo retroviral gene transfer to those cell types that can be readily accessed, maintained and manipulated in culture, and reimplanted, e.g., hematopoietic cells, skin fibroblasts, and hepatocytes.

On the other hand, adenoviral vectors have been shown to efficiently infect many cells types in vivo by direct injection. However, as the adenoviral vector remains episomal and does not integrate into the host cell genome, transgene expression is transient. The utility of adenoviral vectors is further limited by cellular and humoral immune responses against wild type adenovirus gene products, which appear to be expressed at low levels in the transduced cells due to "leaky" expression despite deletion of the E1 regulatory region (Engelhardt et al., 1993; Yang et al., 1995). Once sensitized, a neutralizing antibody response usually precludes repeat administration by the same vector, and adenovirus-infected cells are soon eliminated by cytotoxic T lymphocytes after transduction (Roessler et al., 1995; Yang et al., 1995). Thus, neither type of virus vector can achieve efficient and long term transduction by direct injection in vivo.

Another virus vector which has been considered is the adeno-associated virus (AAV) (Flotte et al., 1993). AAV was initially thought to be advantageous because it appeared to efficiently infect non-dividing cells (Flotte et al., 1994), and would also undergo site-specific integration into the host cell genome, resulting in long term transduction. However, although these do appear to be attributes of wild type AAV, it seems that these characteristics may not be associated with replication-defective AAV vectors, from which the AAV structural genes, especially the rep gene, have been deleted (Halbert et al., 1995). Other disadvantages of the AAV system have been the limited packaging capacity, only about 4 kilobases, of the vector, and the difficulty of making high titer AAV stocks.

Retrotransposons are mobile genetic elements that insert into new genomic locations by a mechanism that involves reverse transcription of an RNA intermediate. Among the most well-characterized human retrotransposons are L1 elements or LINEs (long interspersed nuclear elements); these non-LTR elements are present in approximately 100,000 copies in the human genome, although 97% of these are functionally inactive due to truncations and rearrangements, and of the remaining 3000 or so full length L1 elements (Singer et al., 1993), it has been estimated that only about 1.5–2.5%, i.e., 30 to 60 copies, are active in retrotransposition (Sassaman et al., 1997). A 6 kb L1 consensus sequence has been derived by sequence analysis of multiple elements (Scott et al., 1987), containing a 5' untranslated region with an internal promoter (Minakami et al., 1992; Swergold, 1990), two non-overlapping reading frames (ORF 1 and ORF 2), a 3' untranslated region and 3' polyadenylated tail; ORF 1 encodes a 40 kD nucleic acid binding protein that co-localizes with L1 mRNA in a cytoplasmic complex (Hohjoh and Singer, 1996; Holmes et al., 1992), while ORF 2 encodes a protein with reverse transcriptase (RT) activity (Hattori et al., 1986; Xiong and Eickbush, 1990) and an N-terminal endonuclease (EN) domain (Feng et al., 1996). Recently, it has been demonstrated that a reporter cassette, with a selectable marker gene driven by the SV40 promoter, can be inserted in reverse orientation into the 3'untranslated region of L1 elements, and when transfected into cells as an EBNA/oriP-containing episomal plasmid, this system can be used to detect retrotransposition events (Moran et al., 1996; Sassaman et al., 1997). The human L1/reporter element was also active in mouse fibroblasts, suggesting that cellular factors involved in retrotransposition are conserved (Moran et al., 1996). Furthermore, this system was used to characterize novel human L1 sequences that were screened from a genomic library; one of these, L1.3, retrotransposed at a considerably higher frequency, about 1 retrotransposition event scored per 150 cells containing the episomal plasmid (Sassaman et al., 1997). In fact, the actual frequency is probably even higher, as the assay system scored only retrotransposition events occurring in cells that had been pre-selected for the presence of the full length episomal plasmid. Interestingly, it was found that the promoter in the 5' untranslated region could be replaced with the CMV promoter without significantly affecting the retrotransposition frequency, and that the 3' untranslated region could be completely deleted without any deleterious effect. When some of the integration sites of the L1/reporter element were cloned and the 5' junctions sequenced, the elements were found to have been variably truncated 5' of the selectable marker gene. This results in an integrated element that is presumably incapable of further retrotransposition, as: 1) the 5' promoter is truncated, thus no mRNA intermediate would be transcribed in the forward orientation; 2) the essential ORF (at least ORF 1, and in some cases ORF 2 also) functions are deleted; and 3) even if the ORF 1 and ORF 2 gene products were to be provided in trans, it has been suggested that the retrotransposition process might be designed to ensure that only mRNA that is in cis with the ORFs is preferentially retrotransposed, perhaps by interaction of the nascent ORF 2 protein with the polyA tail of its own transcript during translation (Boeke, 1997).

Although use of retrotransposons as gene delivery vehicles has been previously suggested (Hodgson et al., 1997; Kingsman et al., 1995), and in fact retrotransposons such as rat VL30 elements have been found capable of being packaged and transmitted by MLV (Chakraborty et al., 1994; Torrent et al., 1994), thus far the efficiency of delivering retrotransposon-encoded sequences to target cells has been the rate-limiting step.

Thus, heretofore there has been no optimal method for direct gene transfer and permanent transduction of quiescent tissues in vivo. Although retroviral gene transfer is currently one of the most commonly used methods for delivery of therapeutic genes, it suffers from problems such as relatively low titers and inability to transduce non-dividing cells; conversely, although adenoviral vectors and non-viral lipid-DNA conjugate vectors offer advantages such as high titers and the ability to transduce quiescent cells, neither is capable of efficient integration or permanent transduction. Furthermore, other integrating elements such as retrotransoposons and AAV have been modified for use as vectors, but these systems suffer from the lack of an adequate delivery system or simple methods for production of high titer preparations.

A different approach that has been taken in the design of vectors suitable for gene therapy is the combination of elements from distinct viral vectors. Insertion of retroviral structural genes into Herpes simplex virus (HSV) (Savard et al., 1997) has been described. In this case, only retroviral structural genes were inserted into the HSV carrier, which was used to mobilize a retroviral vector sequence already integrated into an indicator cell line.

Insertion of retroviral structural genes and vector constructs into adenovirus (Bilbao et al., 1997) has been reported; however, retroviral structural genes and retroviral vector constructs had to be inserted separately into standard E1-deleted adenovirus vectors (Bilbao et al., 1997), reflecting the limited cloning capacity, about 7 kb, of the adenovirus vectors used. Adenoviruses carrying the retrovirus structural genes and those carrying the retroviral vector constructs were mixed together to achieve co-infection by both types of adenovirus carriers and thus co-expression of retroviral structural gene and vector constructs, resulting in the secondary production of fully assembled, functional retroviral vectors.

Insertion of retroviral structural gene sequences into adenoviral vectors to produce a hybrid construct previously has also been described as a means to achieve efficient transient expression of packaging proteins, particularly for high titer production of vectors pseudotyped with the VSV-G envelope protein, which is toxic to cells and is usually difficult to express in stable packaging cell lines without tight regulation (Yoshida et al., 1997). Other groups have reported similar approaches for efficient production of AAV vectors, by insertion of AAV structural gene or vector sequences into adenovirus-based hybrid expression systems (Fisher et al., 1996; Thrasher et al., 1995). There has been one report describing the production of hybrid vectors consisting of AAV sequences inserted into a Herpes simplex virus (HSV) amplicon for use as a novel gene delivery vehicle (Johnston et al., 1997). Nevertheless, the applicability of retrovirus sequences as inserts within the context of a larger heterologous virus as a vector for gene delivery was heretofore unknown.

Recently, helper-dependent adenoviral vector systems have been developed; the first such system was originally reported by one of us in 1995 (Mitani et al., 1995) and consisted of a reporter gene cassette inserted in an adenoviral genome that had been deleted of many of its structural elements, retaining the inverted terminal repeat (ITR) and packaging signal sequences. Subsequently, a 28 kb vector DNA containing the full length dystrophin gene, with only 360 bp of adenoviral DNA including the replication origin and the packaging signal, was successfully rescued and propagated in adenoviral virions in the presence of helper virus (Clemens et al., 1996; Kochanek et al., 1996). In this system, all the coding sequences that could be toxic or immunogenic to the host were thus removed from the vector DNA. Although some contaminating helper adenovirus is still present in preparations of helper-dependent vectors, cesium chloride gradient separation has allowed purification of the helper-dependent vectors with residual helper virus present at levels of less than 1% (Kochanek et al., 1996; Mitani et al., 1995), and recently reported refinements in the packaging system appear to reduce the level of helper virus contamination even further, to less than 0.01% (Lieber et al., 1996; Parks et al., 1996).

Another advantage of this system is expanded cloning capacity (up to 38 kb) of foreign DNA into the vector. Interestingly, the minimal packaging size requirement was previously defined as 25 kb or so (Mitani et al., 1995); however, it has recently been shown that smaller vector constructs can also be packaged if concatemerization of the vector sequence occurs, resulting in a multimeric size that is within the 27 to 38 kb packageable size range (Parks and Graham, 1997). This expanded capacity is quite advantageous in the case of large genes; as mentioned above, helper-dependent adenoviral vectors recently have been used to deliver the full-length (14 kb) dystrophin gene into skeletal muscle in cell culture and in vivo (Clemens et al., 1996; Haecker et al., 1996). It is noteworthy that the helper-dependent dystrophin adenovectors appear to elicit no inflammatory reaction in vivo. This lack of inflammatory reaction correlated with prolonged expression of the dystrophin transgene, although there have been reports of both shortened and lengthened transgene expression with other deleted adenovector systems (Gao et al., 1996; Kaplan et al., 1997; Lieber et al., 1996). In spite of the success with helper-dependent adenoviral vectors, this approach is still limited by the inherent lack of stable integration.

The present invention incorporates integrating elements such as retrotransposon vectors as inserts within the context of high capacity helper-dependent adenovirus vectors, and thus constitutes a novel type of hybrid vector system that has not previously been described in the literature.

SUMMARY

The invention provides hybrid vectors suitable for the delivery of genetic material or nucleic acid molecules into a cell. The hybrid vectors comprise an adenoviral capsid that delivers a helper-dependent nucleic acid molecule encoding an adenoviral region and other inserted heterologous vector elements such as a transposon region.

The adenovirus capsid that encoats the nucleic acid molecule is provided by a helper adenovirus. The helper adenovirus can be any adenovirus or adenovirus vector, derived from any serotype, that can provide adenovirus early and late proteins necessary for replication and packaging of the helper-dependent nucleic acid molecule, which is itself incapable of being replicated or packaged in eukaryotic cells in the absence of the helper adenovirus.

The adenovirus region of the nucleic acid molecule of the hybrid vector comprises a helper-dependent or "gutted" adenoviral vector. Such vectors lack genes necessary for replication and packaging of the adenovirus and are unable to replicate in the absence of the helper adenovirus that supplies the necessary adenoviral structural elements. The adenoviral region therefore can substantially lack nucleic acid sequences encoding adenoviral structural genes. Nucleic acid molecules of the hybrid vectors contain within the adenoviral region a pair of adenoviral inverted terminal repeat sequences as well as a packaging signal from the adenovirus. The elements of the adenoviral region can be those found in any adenovirus, substantially similar sequences, or combinations of such sequences. In one embodiment, adenoviral regions have sequences substantially similar to those found, for example, in adenovirus serotype 2. In another embodiment, adenoviral regions have sequences substantially similar to those found in adenovirus serotype 5.

The hybrid vector system of the invention transduces cells by a two stage mechanism. In the first adenoviral stage, the inserted vector elements, included in the helper-dependent nucleic acid molecule to be delivered, will be carried by the adenoviral capsid, to then be expressed in the target cells and thereby direct the production of the second stage vectors.

Nucleic acid sequences of interest can be any nucleic acid molecule for which delivery is desired, including nucleic acids encoding, for example, genes, cDNAs and various RNA species including, for example, ribozymes, antisense sequences and structural RNAs.

In one embodiment, the inserted vector elements of the invention contain a second stage retrotransposon region. The transposon region has a sequence substantially similar to that of any known retrotransposon or DNA transposon, and can also contain heterologous elements within the transposon region. Such transposons permanently integrate into the genome of the initially transduced cells, and the heterologous elements are contained within the transposon regions, and hence will also be integrated during this process. The heterologous elements can also contain promoter, polyadenylation signal, and/or any other sequences necessary for expression of an operably linked sequence of interest also contained within the heterologous element.

BRIEF DESCRIPTION OF THE DRAWINGS

FIG. 6A shows the results of a PCR analysis of individual clones using neoR-specific primers. Lane 1 shows a 1 kb ladder; Lanes 2–6 are individual $G418^R$ clones; lane 7 is a HeLa cell negative control; and lane 8 is an unspliced vector control.

FIG. 6B shows a Southern blot analysis of individual clones probes with a neoR fragment: lanes 1–3 are individual G418R clones; lane C is a negative HeLa DNA control; and lane L is a linear vector control.

DETAILED DESCRIPTION

Definitions

Figure 1:
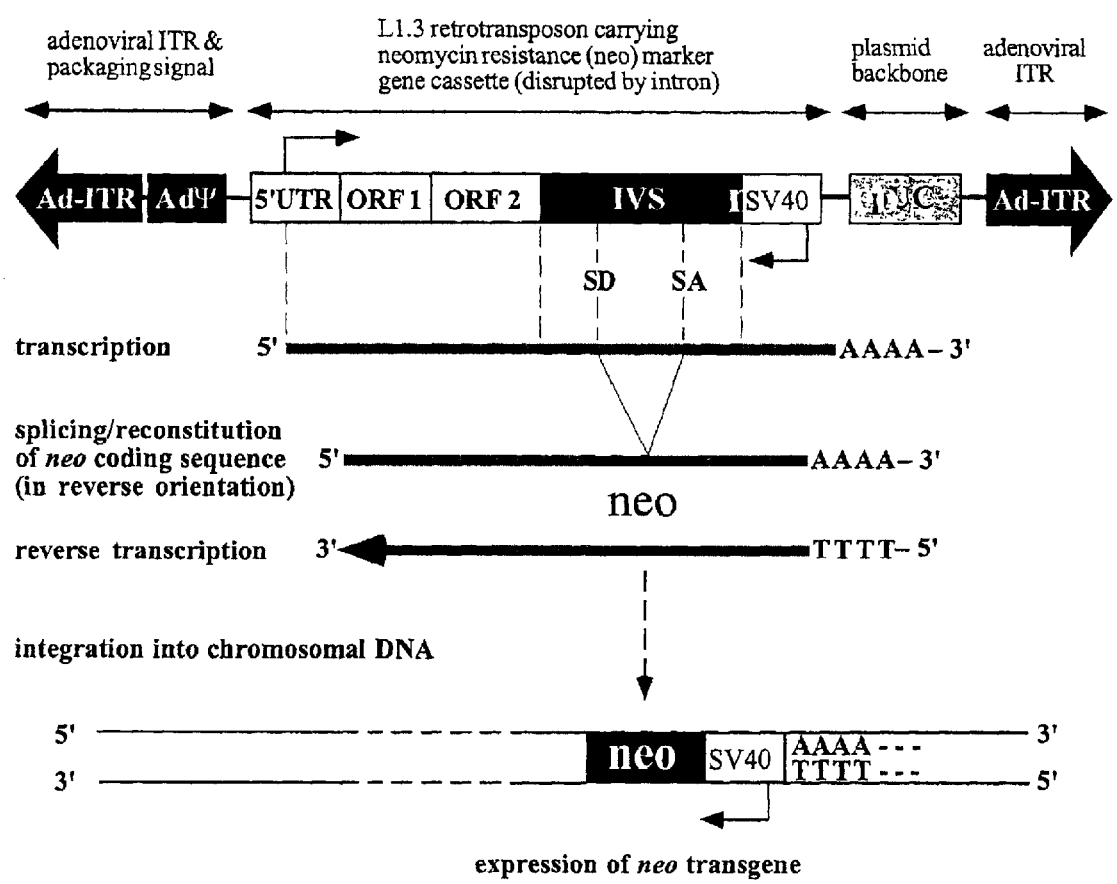
FIG. 1 illustrates the retrotransposon-adenovirus hybrid vector construct RAd-L1.3 neo.

The term "operably linked" refers to two or more nucleic acid sequences that are positioned such that a functional relationship is maintained. Operably linked sequences can be adjacent, or distal to one another in a nucleic acid molecule. For example, a promoter may function to regulate expression of a gene though it is located distally from the gene.

The term "region" as used herein defines a portion of a nucleic acid molecule or nucleic acid sequence that has a common function or a common origin, i.e. regions are derived from the same class of virus. Because a region can be interrupted, for example, by a nucleic acid molecule to be delivered or by another region, regions encompass contiguous and non-contiguous nucleic acid sequences.

"Substantially similar" as used herein describes a relationship between nucleic acid sequences wherein the sequences are at least about 50% identical, preferably 70% identical and more preferably 90% identical when the sequences are aligned such that identical residues are maximized. A substantially similar sequence includes one in which codons have been changed to facilitate expression in a particular host organism. Codon usage preferences are known to one of skill in the art of molecular biology.

Variants of known sequences coding for proteins are preferred that result in the substitution of amino acids with amino acid residues with similar characteristics. A preferred substitution for aspartic acid, for example, would be another acidic residue, i.e. glutamic acid. One of skill in the can determine similar preferred substitutions for hydrophobic, basic, large and small amino acid groups.

Adenoviral Vectors

Hybrid vectors are provided that contain both adenoviral regions and secondary elements such as retroviral regions or transposon regions. Such hybrid vectors are novel systems for the delivery of genetic material or nucleic acid molecules to a cell. Such vectors can be efficient enough for direct in vivo application and can be capable of long term transduction. The term vector can be used to describe both the nucleic acid component of a vector as well as nucelic acids packaged as viral particles.

In this hybrid virus system, an adenoviral vector delivers the secondary vector elements into the host nuclei. As described above, adenoviral vectors can infect non-dividing cells efficiently and can be prepared as a high titer stock. Thus, this system is currently considered as the most efficient in vivo gene delivery system. To circumvent the immunogenicity problem of first-generation (E1-deleted) adenoviral vectors, which result in rapid clearance of vector-transduced cells, a preferred adenoviral region for inclusion in the hybrid vector is a helper-dependent adenoviral vector. Not only is the immunogenicity minimized with this system, but also large or multiple inserts can be delivered via this system. Thus, in the present invention, we utilize the machinery of retroviruses and retrotransposons, delivered in the context of a helper-dependent adenovirus vector, to achieve stable integration and permanent transduction.

The adenovirus region of the hybrid vector is a helper-dependent or "gutted" adenoviral vector. Such vectors lack genes necessary for replication of the adenovirus and are unable to replicate in the absence of a helper virus that supplies necessary adenoviral structural genes. The adenoviral region substantially lacks nucleic acids encoding adenoviral structural genes. Hybrid vectors contain within the adenoviral region a first and second adenoviral inverted terminal repeat sequence as well as a packaging signal from the adenovirus. The elements of the adenoviral region can be those found in any adenovirus, substantially similar sequences, or combinations of such sequences. In one embodiment, adenoviral regions have sequences substantially similar to those found, for example in adenovirus serotype 2. In another embodiment, adenoviral regions have sequences substantially similar to adenovirus serotype 5. The adenoviral inverted terminal repeats (ITRs) can be organized in any functional orientation within the hybrid vector. For example, the ITRs can be organized in a head to head or in a tail to tail orientation. ITRs preferably surround the second stage insert. The adenoviral packaging signal is preferably located adjacent to one of the ITR sequences.

Transposon Elements Second Stage Inserts

Hybrid vectors can also contain a transposon region. A transposon region can be any suitable DNA transposon or retrotransposon sequence or a sequence substantially similar to that of any known retrotransposon or DNA transposon. Such transposons permanently integrate into the genome of the initially transduced cells. Retrotransposon-derived transposon regions contain a sequence encoding a capsid-like protein and a sequence encoding a reverse transcriptase. The retrotransposon-derived transposon region also contains a promoter sequence operably linked to the capsid-protein encoding sequence and to the reverse-transcriptase encoding sequence. DNA transposon-derived transposon regions contain inverted or direct repeat sequences flanking the sequence to be integrated, and also contain sequences encoding a transposase which catalyzes the excision of the transposon from its original location and promotes its reintegration elsewhere, and a promoter sequence operably linked to the transposase encoding sequence. The transposon region of the hybrid vector can also contain a heterologous element that encodes a sequence of interest to be integrated into the host cell genome along with the transposon during the process of transposon integration. The sequence of interest can also be operably linked to a promoter, polyadenylation signal, and other sequences within the heterologous element in order to facilitate its expression in the host cell.

In one embodiment, the transposon regions is derived from a retrotransposon vector which is an L1 retrotransposon containing a heterologous element containing a reporter gene expression cassette. By insertion of such an L1/reporter element into the helper-dependent adenovirus system, the retroelement can be efficiently delivered to the adenovirus-transduced target cells, and subsequently retrotransposed and stably integrated into the DNA of these same cells. Although the frequency of retrotransposition may be as low as 1 in 150 of the adenovirus-transduced cells, since adenovirus titers can reach as high as $10^{10}$ to $10^{11}$ pfu per ml, this will still result in an integration frequency that compares favorably with that of retroviral titers. In fact, in addition to the high transduction efficiency achievable with adenovirus vectors, the adenoviral transgene copy number increases with increasing multiplicity of infection (MOI), and so the level of retrotransposon expression per cell may increase as well, leading to higher frequencies of retrotransposition. Furthermore, as the integrated L1 elements will often end up with truncated ORF 1 and ORF 2 sequences at their 5' ends (Moran et al., 1996), we suggest that this system is relatively safe, and that there will be little chance of promiscuous recurrent transposition leading to unacceptable frequencies of insertional mutagenesis. An advantage of such a retrotransposon-adenovirus hybrid vector system is that the same cell that was originally transduced by the first-stage adenovirus vector will itself be permanently transduced by the second-stage L1 retrotransposon vector, unlike the retrovirus-adenovirus hybrid vector system in which the initially transduced cell serves as a packaging intermediate for production of the second-stage retroviruses that then permanently transduce adjacent cells. An additional potential advantage is that the L1 elements are normally present endogenously in all human cells, thus in combination with the helper-dependent adenovirus vector which is itself deleted of all the adenoviral structural genes, this may provide a high titer adenovirus-based system that is capable of stable integration into the host cell genome, yet will not induce a Class I immune response directed against the vector itself.

It should be noted in this context that the present invention can be practiced not only with retrotransposon elements as the secondary inserts (described in detail in Examples 1 and 4–6), but, in another embodiment, with DNA transposon elements. In the case of the latter, the transposon vector element is released from the first stage adenoviral genome and inserted into the target cell chromosome by a simple "cut-and-paste" mechanism encoded by the transposon structural genes. DNA transposons suitable for incoporation into hybrid vectors include those substantially similar to the Tc1 family of DNA transposons (Plasterk, R. H., 1996; Plasterk, R. H., 1999). Such transposons include those with sequences substantially similar to naturally occuring transposons such as Mariner (Gueiros-Filho and Beverly, 1997) as well as those substantially similar to natural sequences such as Sleeping Beauty (Ivics, Z. et al., 1997).

Genetic Material

The vectors of the invention are suitable for the delivery of any genetic material or nucleic acid molecule of interest to a cell. The hybrid vectors can contain a nucleic acid sequence to be delivered to a cell. For example, a gene or DNA sequence encoding a protein product can be such that expression of said gene relieves a deficiency in the target cell or within the organism. The nucleic acid molecule to be delivered is not limited to genes and protein encoding sequences. Other sequences suitable for delivery include RNA sequences such as structural RNA molecules, RNA molecules designed to bind to particular cellular components, e.g. aptamers, RNA molecules that possess catalytic activity (ribozymes) and RNA molecules that bind to specific mRNA molecules (antisense molecules).

For optimization and laboratory usage, a marker gene is the preferred genetic material to be included in hybrid vector. A marker gene is detectable by any number of techniques, including by fluorescence detection, calorimetric detection or immunologic detection. One of skill in the art can determine any number of suitable marker genes for use with the invention. Particularly preferred marker genes are expressed as fluorescent products such as green fluorescent protein and variants thereof.

Cells

Cells of the invention include cells from any organism. Preferred cells of the invention are animal cells. More preferred cells of the invention are mammalian cells. Vectors of the invention can be used to infect cells in vivo or ex vivo. Cells encompasses cultured cells as well as cells within an organism. Suitable cells can be, for example, human, cow, horse, pig, rabbit, rat or mouse cells. Choice of suitable vector components as described herein can be used to determine the host range of the hybrid vectors.

General Techniques

The construction of vectors from the elements or regions described is within the ability of one skilled in the art of molecular biology. Hybrid vectors of the invention are often constructed in the form of plasmids that are linearized before infection of initial target cells. General molecular biology techniques may be used, such as those described in Sambrook, J. et al., 1989, Molecular Cloning: A Laboratory Manual, Cold Spring Harbor Laboratory, NY; or Ausubel, F. M. et al., 1989, Current Protocols in Molecular Biology, John Wiley & Sons, New York N.Y., both of which are incorporated herein by reference in their entirety. More specifically, manipulations of viruses and of viral vectors is described in, for example, Hitt, M. Human adenovirus vectors for gene transfer into mammalian cells. Adv Pharmacol. 1997; 40:137–206; Becker, T. C. et al. Use of recombinant adenovirus for metabolic engineering of mammalian cells. Methods Cell Biol. 1994; 43 Pt A: 161–89, and Graham, F. L. and Prevec L. Manipulation of adenovirus vectors. Molecular Biotechnology 1995; 3:207–220.

Helper Adenoviruses

Because the hybrid vectors of the invention are helper-dependent, it is necessary to use a helper adenovirus to package the adenovirus particle. A number of helper adenovirus vectors are known. A preferred helper adenovirus is defective in one or more genes and/or other sequences or has been engineered such that it is unlikely to contaminate the prepared adenovirus particles encoded by the hybrid vectors described herein. A particularly preferred helper adenovirus system is one that uses the Cre-Lox system described herein.

EXAMPLES

Example 1

Construction And Production Of Retrotransposon-Adenovirus Hybrid Vectors

We also describe the process of constructing retrotransposon-adenovirus hybrid vectors. Our collaborators, Dr. H. Kazazian and Dr. J. Moran (U. Penn), have generously provided us with an L1 retrotransposon element/reporter gene construct that has been described above ((Moran et al., 1996), see Background). This element, L1.3, has the highest retrotransposition frequency of all the human LINEs tested, and the reporter gene cassette is inserted into its 3' untranslated region in the reverse (antisense) orientation. The reporter cassette consists of the $neo^R$ gene, which is disrupted by an intron (IVS 2 of the g-globin gene) in the opposite transcriptional orientation with respect to the $neo^R$ gene (i.e., intron is in the sense orientation with respect to the overall L1 construct), and is flanked by SV40 promoter and polyA sequences (see FIG. 1). This arrangement ensures that G418 resistance will only arise if the L1 retroelement is transcribed from its 5' promoter, the mRNA is spliced to remove the intron disrupting the $neo^R$ coding sequence, the element is then reverse transcribed and re-integrated into chromosomal DNA, and now intact $neo^R$ gene is expressed from the SV40 promoter in the antisense direction. Thus only actual retrotransposition events will be scored. In contrast, transcripts originating directly from the SV40 promoter cannot be spliced, an intact $neo^R$ gene product cannot be produced, and the cells will not become G418 resistant and therefore will not be scored in this assay.

This L1 retrotransposon/reporter cassette system is approximately 8.1 kb in size (6 kb L1.3 retrotransposon sequence +2.1 kb $neo^R$ reporter gene cassette). In order to use the helper-dependent adenovirus system as a first-stage carrier for this retrotransposon vector, we add flanking adenoviral ITRs and the adenovirus packaging signal to the L1 construct. The second-stage retrotransposon produced after adenovirus vector transduction therefore mediates proper splicing, reverse transcription, and stable integration of the $neo^R$ transgene. This construct design is shown in FIG. 1.

As previously described, the retrotransposon-adenovirus hybrid construct pRAd-L1.3neo is co-transfected into $2 \times 10^6$ 293 cells along with the helper adenovirus genome Ad-hprt by calcium phosphate precipitation. The 293 cells are overlayed with agar, and incubated until plaque formation is observed, about 5 days later. Cell lysate from a total of 100 plaques is collected and individually re-inoculated on fresh 293 cells in 96-well plates. After incubation for 48 to 72 hours, these cells are detached from the wells using a non-enzymatic buffer containing 2 mM EDTA in phosphate-buffered saline, lysed by 3 freeze-thaw cycles, and after spinning down cell debris, the supernatant is used to further amplify each virus isolate by individually re-inoculating fresh 293 cells in 24-well plates. The amplification procedure is repeated using progressively larger plates until adequate stocks of adenovirus are obtained for each plaque originally isolated.

Testing Transduction Efficiency And Stable Integration Of The Transgene In Cell Culture.

About 48 to 72 hours after inoculation, when cytopathic effects can be observed but prior to complete cell lysis, the 293 cells in which individual isolates of adenovirus are being amplified are harvested by repeated freeze-thaw cycles to lyse the cells. The cell debris is pelleted, and the supernatant is used as the crude virus preparation for subsequent NIH3T3 infection. Although the retrotransposon component of the hybrid vector presumably will integrate the properly spliced $neo^R$ transgene into the genome of the 293 cells used for amplification, the presence of the helper virus will cause cytopathic effects and result in cell death of clones even if they are G418 resistant. Again, as adenovirus does not replicate in NIH3T3 cells, it should therefore be possible to test for retrotransposition and transgene expression by G418 selection in NIH3T3 cells. Furthermore, genomic DNA can be isolated from the transduced NIH3T3 cells and analyzed by Southern blot using probes against the retrovirus vector transgene sequences, in order to confirm stable integration of the transgenes. The neo$^R$ transgene must be properly spliced in order to remove the disrupting intron sequence, and so any G418 resistant cells should be derived from authentic retrotransposition events. This can be confirmed by the size of the transgene sequence detected on Southern blots, and by PCR using neomycin sequence primers that span the intron insertion site.

Example 2

Testing the Transduction Efficiency and Duration of Transgene Expression in the Liver by Tail Vein Injection of R-Ad Vectors in C57b1/6 Mice Hybrid retrovirus-adenovirus or retrotransposon-adenovirus vectors are tested for their ability to mediate efficient and stable transduction in vivo, and for their immunogenicity, using an immunocompetent C57b1/6 mouse model. In vitro systems using pure populations of cultured cell monolayers are inadequate to address issues relating to the efficiency of gene delivery in the context of the mixed quiescent and proliferating cell populations present in vivo and the architectural complexity of intact tissues. Furthermore, other parameters such as the optimal route and method of delivery, dose response and optimal titer, safety or toxicity of high dose virus preparations, duration of expression in transduced cells in situ, and the possibility of an immune response, can only be investigated in vivo.

Each hybrid vector preparation is harvested from 10 inoculations of 293 cells in T175 flasks, which normally produce a titer of $10^{9-10}$ per ml per flask. The cells are lysed by 3 cycles of freeze-thawing, the cell debris pelleted, and the helper-dependent virus purified by cesium chloride gradient centrifugation. The animals are first anesthetized with an inhalational general anesthetic such as halothane or metaphane, and the induction of an adequate level of anesthesia confirmed by areflexivity to stimuli such as tail pinch. Control infections using GFP-negative vectors are performed in parallel. In addition, standard E1-deleted first generation adenovirus vectors carrying the GFP marker gene are used as a "positive" control series for each experiment. Virus preparations are injected by tail-vein injection and assayed for transduction in the liver.

Four days, fourteen days, and twenty-one days after administration of the virus preparations, transduction efficiency and immune response against the vectors is assessed. At this point, the animals are humanely sacrificed by an overdose of inhalational anesthetic followed by cervical dislocation, in accordance with the recommendations of the Panel on Euthanasia of the American Veterinary Medical Association. Tissues are then harvested, including liver specimens for fixation, staining and histological examination, and splenocytes collected for CTL assays (see below). Tissue samples are snap frozen in liquid nitrogen and frozen sections cut on a cryostat, mounted on polylysine-coated glass slides, and examined by UV fluorescence microscopy for GFP expression. Sections are also fixed with 4% paraformaldehyde and 0.1% glutaraldehyde in PBS (pH 7.4), and stained with hematoxylin-eosin for histological examination to assess whether any inflammatory infiltrate is present. The efficiency and immunogenicity of the hybrid vectors is assessed by comparison with samples from the negative and positive control adenovirus experiments. Some tissue samples can also be lysed for genomic DNA extraction, and transgene integration assayed by Southern blot.

Example 3

A Cre-lox System For Helper-Dependent Virus Production

During the process of expanding plaque isolates of RAd-g1ZDGFP in progressively larger scale cultures for further experiments, we encountered technical difficulties in the amplification process, as growth of the helper-dependent form is quite poor compared to the helper virus. Therefore, a new system for amplification of helper-dependent viruses, using 293-cre cells, has been established, using reagents obtained from Merck. Similar helper adenovirus systems are described in, for example, Ng. P. et al. (1999) A high-efficiency Cre/loxP-based system for construction of adenoviral vectors. Hum. Gene Ther. 10:2667–72.

Figure 2:
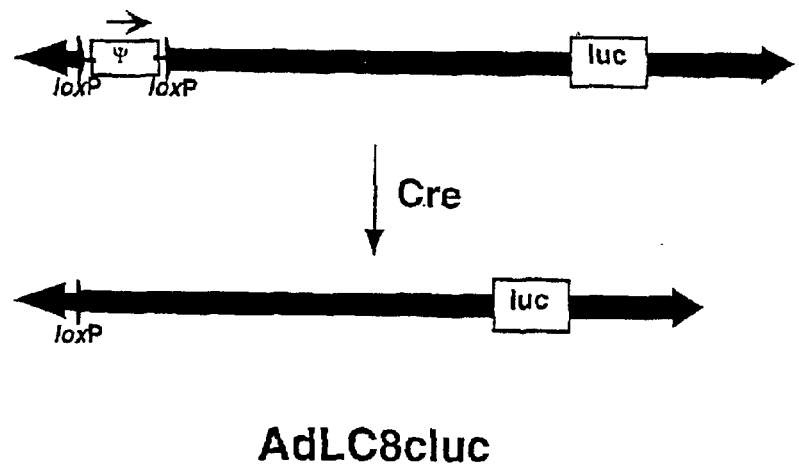
FIG. 2 illustrates recombination of loxP site-containing helper adenovirus vectors in Cre recombinase expressing cell lines. The packaging signal (Ψ) of the helper adenovirus AdLC8cluc is flanked by loxP sites. Upon introduction into 293Cre4 cells, the Cre recombinase removes the packaging signal, thus inhibiting the ability of the helper adenovirus to propagate.

This system confers a growth advantage to the helper-dependent form by using a crippled helper virus which has loxP sites flanking the viral packaging signal (AdLC8cluc). Thus, when grown in 293-derived cell line expressing the Cre recombinase (293Cre4), the helper virus will provide essential viral functions in trans, but its own packaging signal will be efficiently deleted, resulting in more efficient packaging of the helper-dependent construct (FIG. 2). The packaging signal of the helper virus was found to be excised at an efficiency of 80~100% in the 293 Cre4 cells.

For propagating a helper-dependent vector, AdSTKCMVb, we transfected 293 Cre4 cells in 60-mm dishes with pSTK120CMVb DNA, which contains the lacZ reporter gene. Twenty-four hours after transfection, the cells were infected with AdLC8cluc, which contains the luciferase reporter gene, and harvested 72 hr after infection. Viruses were released by freezing and thawing and used for a next round of amplification. At each round of amplification with increasing scale, 293 Cre4 cells were infected with an aliquot of AdSTKCMVb and with AdLC8cluc at an MOI of 1.

Figure 3:
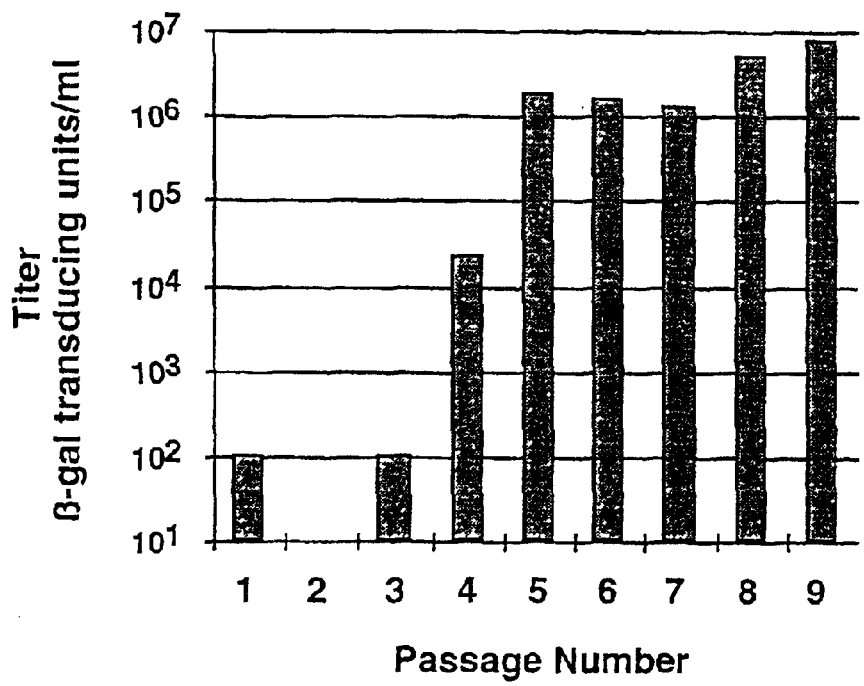
FIG. 3 demonstrates the improved growth of helper-dependent vector using the Cre-lox system. The helper-dependent adenovirus vector AdSTKCMVb was grown with the helper adenovirus A1C8cluc in the 293Cre4 cell system. The bar graph shows the titer of the helper-dependent vector over serial passages. The titer is initially quite low, but eventually reaches $10^{6-7}$ per ml using the Cre-lox system.

During propagation, the titer of AdSTKCMVb was monitored (FIG. 3) by infecting A549 cells with the diluted vector followed by the X-gal staining. The titer was $7.6 \times 10^6$ after 9 rounds of amplification. The structure of the vector was also confirmed by Southern hybridization, and no deletion was found.

Example 4

Construction of Retrotransposon-adenovirus Hybrid Vector PRAd-L1.3neo-GFP

Figure 4:
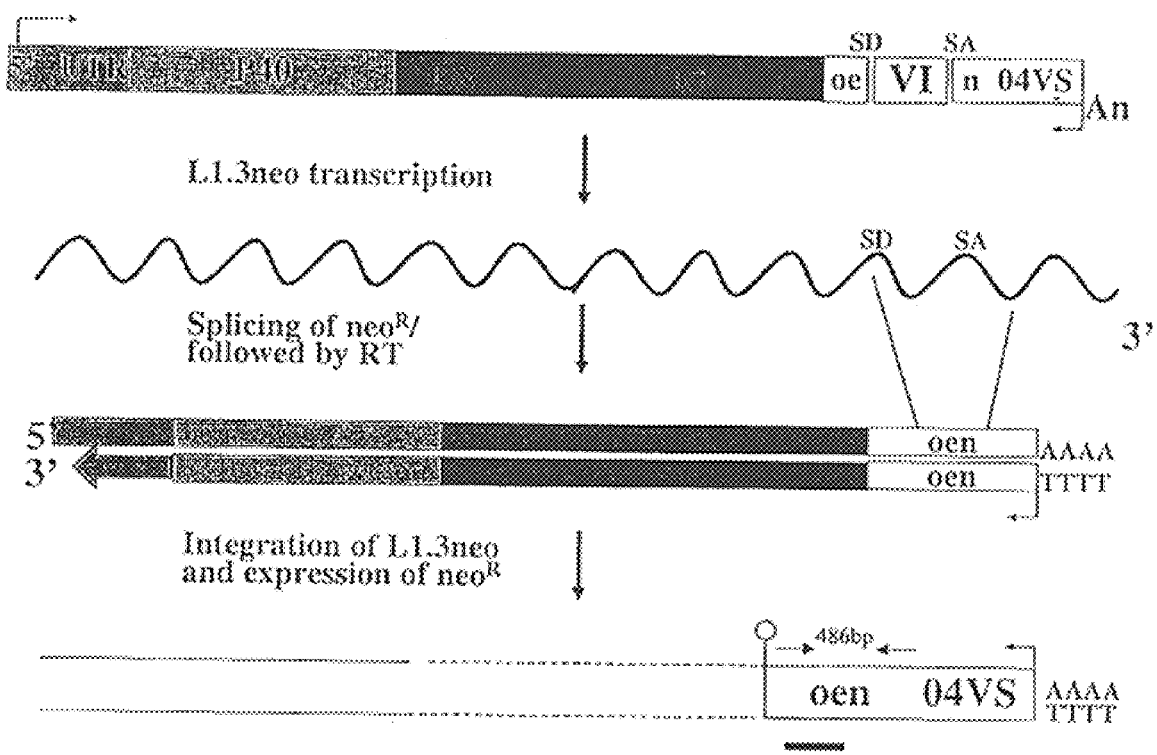
FIG. 4 schematically illustrates the assay used to score retrotransposition events. Successful retrotransposition involves splicing and integration resulting in the formation of a 486 bp reconstituted neomycin resistance gene (neo).

We have constructed a prototype retrotransposon-adenovirus hybrid vector, using an L1 retrotransposon element/reporter gene construct provided by our collaborators Dr. Haig Kazazian and John Moran. This L1 retrotransposon/reporter cassette system is approximately 8.1 kb in size (6 kb L1.3 retrotransposon sequence+2.1 kb SV40 promoter-driven neomycin resistance (neo$^R$) reporter gene cassette). The neo$^R$ cassette is in the reverse orientation from the retrotransposon, and its coding sequence is interrupted by a forward orientation intron sequence. This construct will thus result in stable integration and expression of a functional neo$^R$ gene and thus confer resistance to the antibiotic G418 only if correct retrotransposition occurs, by transcription of L1.3 mRNA, splicing of the RNA in the forward orientation, followed by reverse transcription of the spliced form and integration into genomic DNA so that the SV40 promoter can function to drive expression of the now intact $neo^R$ gene (FIG. 4). In order to use the helper-dependent adenovirus system as a first-stage carrier for this retrotransposon vector, we cloned the L1.3-neo cassette into the plasmid pSTK-GFP, which contains the adenoviral ITRs and packaging signal, along with a GFP marker gene driven by the CMV promoter and C346 cosmid stuffer sequence. The GFP marker is therefore outside the retrotransposon cassette but will still serve as a marker of adenoviral transduction. The resultant plasmid construct was designated HDL1.3 neo.

Figure 5:
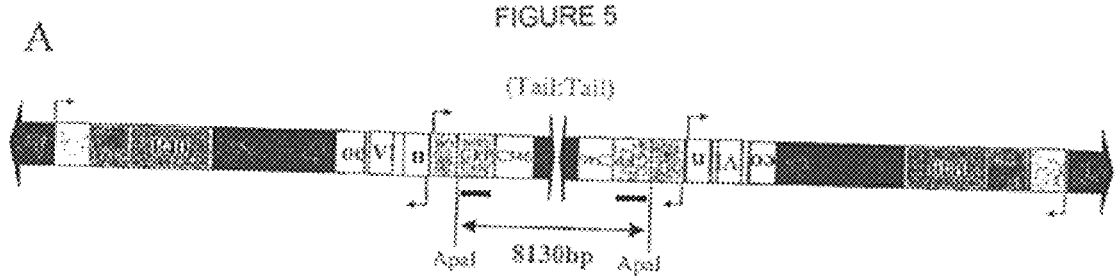
FIG. 5A shows a schematic view of hybrid vector HDL1.3neo.
FIG. 5B shows a Southern blot of crude HDL1.3neo DNA probed with GFP cDNA. The results indicate that HDL1.3neo is a mixture of concatemers.
Figure 5:
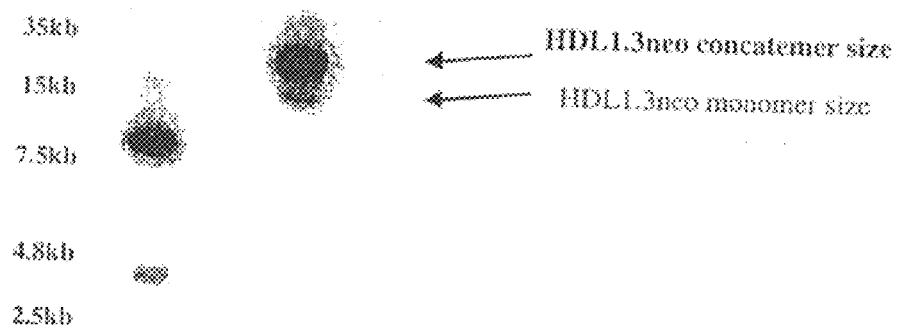

After propagation of the HDL1.3 neo vector in the cre-lox system as above, Southern blot analysis of the adenoviral Hirt prep DNA was performed after Apa I digest using a GFP-specific probe to determine its genomic structure. As shown in FIG. 5, in this case the hybrid vector obtained appeared to predominantly consist of a tail-to-tail concatemer as evidenced by the presence of a characteristic 8 kb band, but an additional 4 kb band was also observed as a minor species, suggesting that a smaller population of head-to-tail concatemers might also be present, thus the HDL1.3 neo vectors obtained represent a mixed population. Interestingly, in addition to a band corresponding to the concatemerized length, a weaker signal corresponding to a monomer-size band was also present in undigested DNA samples, suggesting that in this case, vectors smaller than the previously reported 25 kb "minimal" adenovirus packaging size could also be packaged and propagated, and this could also account for the 4 kb band upon Apa I digest. Expression of the CMV-GFP marker cassette in the retrotransposon-adenovirus hybrid vector was confirmed by flow cytometric analysis of 293 cells and infected HeLa cells.

Example 5

Infection of HeLa Cells with Retrotransposon-Adenovirus Hybrid Vector HDL1.3 Neo The helper-dependent HDL1.3 neo adenovirus was used to infect HeLa cells, and 5 days after infection, the cells were subjected to selection with the neomycin analog G418. A dose-dependent increase in the number of G418-resistant colonies was observed with increasing concentrations of the HDL1.3 neo vector, confirming that the hybrid vector in the infected HeLa cells was mediating successful retrotransposition. A negative control showed no G418 resistant colonies. The retrotransposition frequency obtained in this experiment was calculated to be on the order of 1 in 2150 cells, but this was done with a multiplicity of infection (MOI) of less than 1 (i.e., the ratio of virus to cells was less than 1).

Figure 6:
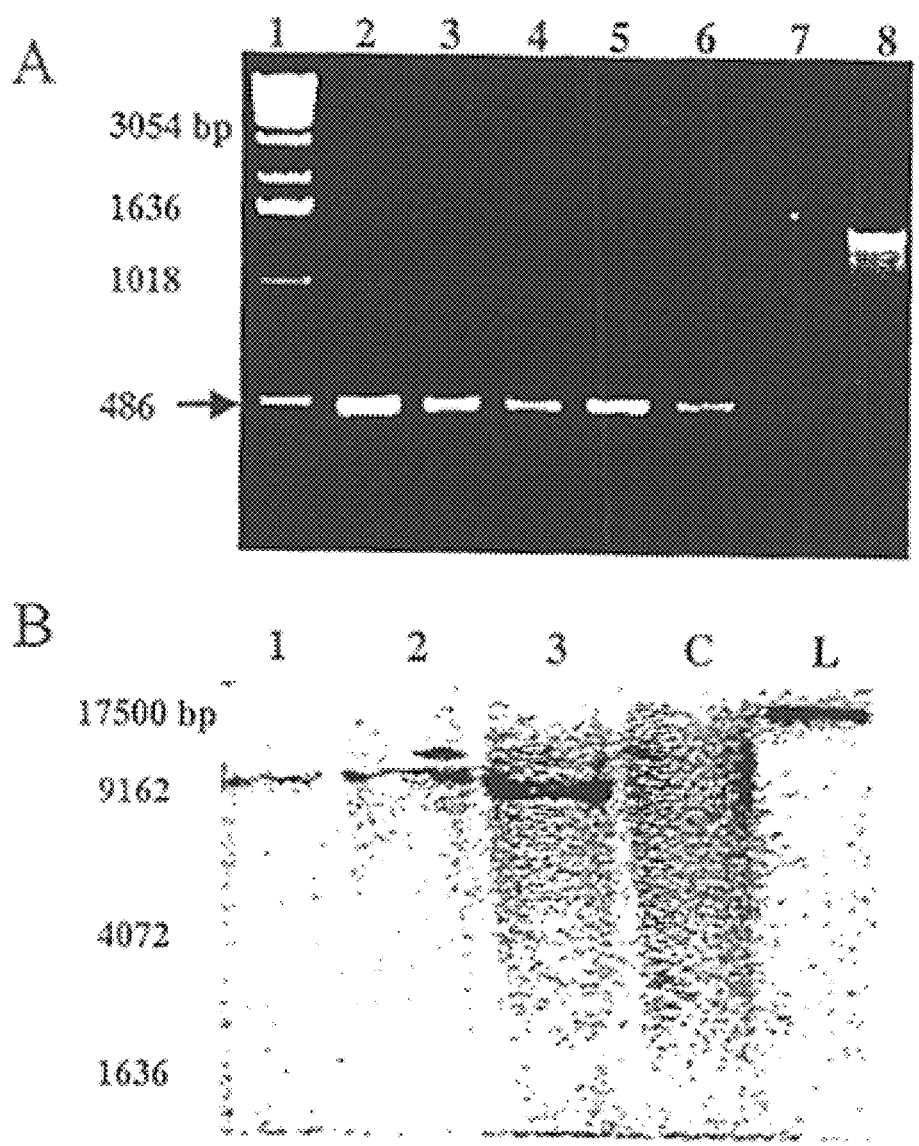
FIG. 6 shows that the neoR transgene is successfully spliced and integrated in individual $G418^R$ clones that had been infected with the HDL1.3neo hybrid vector.

Both PCR and Southern blot analyses of individual colonies surviving G418 selection were performed (FIG. 6). Primers specific for the $neo^R$ gene, and situated at sites flanking the intronic sequence, were used to amplify genomic DNA from individual subclones. The amplified band size corresponded to that of the spliced form, confirming that correct retrotransposition had occurred in these colonies. Furthermore, Southern blots probed with the $neo^R$ sequence showed that genomic integration of the retrotransposon component had indeed occurred.

Example 6

Increasing MOI Results in a Higher Retrotransposition Frequency

Figure 7:
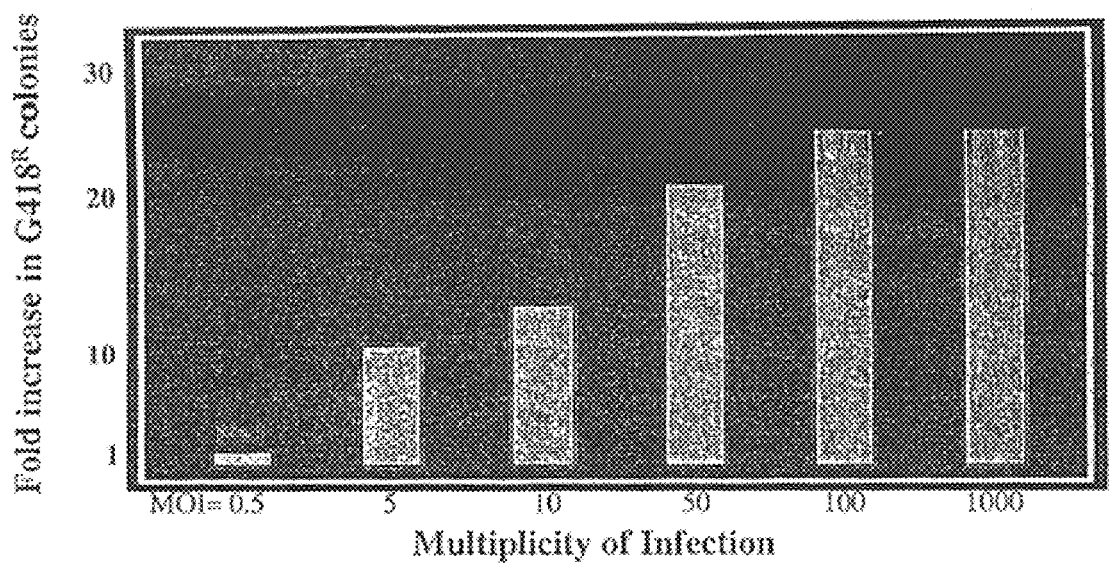
FIG. 7 shows that increasing the multiplicity of infection results in higher retrotransposition frequency. The fold increase in $G418^R$ colonies is graphed versus the multiplicity of infection.

To determine whether increasing the MOI of the adenovirus stage on the target cells would result in a higher retrotransposition frequency, G418-resistant colonies were counted after infection with progressively increasing doses of HDL1.3 neo vector. Up to 25-fold increase in retrotransposition frequency was observed with increasing doses up to a MOI of 100, after which no further increase was observed (FIG. 7).

The foregoing description of the invention has been presented for purposes of illustration and explanation and is not intended to limit the invention to the precise manner of practice described herein. It is to be appreciated therefore, that changes may be made by those skilled in the art without departing from the spirit of the invention and that the scope of the invention should be interpreted with respect to the following claims.

All of the following publications which are cited in the body of the instant specification are hereby incorporated by reference in their entirety.

LITERATURE CITED

Bilbao, G. et al. (1997). Adenoviral/retroviral vector chimeras: a novel strategy to achieve high-efficiency stable transduction in vivo. FASEB J. 11, 624–34.

Boeke, J. (1997). LINEs and Alus-the polyA connection. Nature Genetics 16, 6–7.

Cannon, P. M. et al.(1996). Murine leukemia virus-based Tat inducible LTR replacement vectors: a new system for anti-HIV gene therapy. J. Virol. 70, 8234–40.

Chakraborty, A. K. et al.(1994). Transmission of endogengous VL30 retrotransposons by helper cells used in gene therapy. Cancer Gene Ther. 1, 113–8.

Clemens, P. R. et al. (1996). In vivo muscle gene transfer of full-length dystrophin with an adenoviral vector that lacks all viral genes. Gene Ther. 3, 965–72.

Engelhardt, J. F. et al. (1993). Direct gene transfer of human CFTR into human bronchial epithelia of xenografts with E1-deleted adenoviruses. Nat.Genet. 4, 27–34.

Feng, Q. et al. (1996). Human L1 retrotransposon encodes a conserved endonuclease required for retrotransposition. Cell 87, 905–16.

Fisher, K. J. et al. (1996). A novel adenovirus-adeno-associated virus hybrid vector that displays efficient rescue and delivery of the AAV genome. Hum. Gene Ther. 7, 2079–87.

Flotte, T. R. et al. (1993). Stable in vivo expression of the cystic fibrosis transmembrane conductance regulator with an adeno-associated virus vector. Proc. Natl. Acad. Sci. USA 90, 10613–7.

Flotte, T. R. et al. Am J Respir Cell. Mol. Biol. 11, 517–21.

Gao, G. P. et al. (1996). Biology of adenovirus vectors with E1 and E4 deletions for liver-directed gene therapy. J. Virol. 70, 8934–43.

Gueiros-Filho, F. J. and Beverly, S. M. (1997) Transkingdom transposition of the Drosophila element Mariner within the protozoan Leishmania. Science, 276: 1716–1719.

Haecker, S. E. et al.(1996). In vivo expression of full-length human dystrophin from adenoviral vectors deleted of all viral genes. Hum. Gene Ther. 7, 1907–14.

Halbert, C. L. et al. (1995). Adeno-associated virus vectors transduce primary cells much less efficiently than immortalized cells. J. Virol. 69, 1473–9.

Hattori, M. et al. (1986). L1 family of repetitive DNA sequences in primates may be derived from a sequence encoding a reverse transcriptase-related protein. Nature 321, 625–628.

Hodgson, C. P. et al. (1997). Biosynthetic retrovectoring systems for gene therapy. J. Mol. Med. 75, 249–58.

Hohjoh, H., and Singer, M. F. (1996). Cytoplasmic ribonucleoprotein complexes containing human LINE-1 protein and RNA. EMBO J. 15, 630–639.

Holmes, S. E., Singer, M. F., and Swergold, G. D. (1992). Studies on p40, the leucine zipper motif-containing protein encoded by the first open reading frame of an active human LINE-1 transposable element. J. Biol. Chem. 267, 19765–19768.

Hwang, L. H. S., and Gilboa, E. (1984). Expression of genes introduced into cells by retroviral infection is more efficient than that of genes introduced into cells by DNA transfection. J. Virol. 50, 417–424.

Ivics, Z. et al. (1997). Molecular reconstruction of Sleeping Beauty, a Tc1-like transposon from fish, and its transposition in human cells. Cell 91, 501–10

Johnston, K. M. et al. (1997). HSV/AAV hybrid amplicon vectors extend transgene expression in human glioma cells. Hum. Gene. Ther. 8, 359–70.

Kaplan, J. M. et al. (1997). Characterization of factors involved in modulating persistence of transgene expression from recombinant adenovirus in the mouse lung. Hum. Gene Ther. 8, 45-56.

Kingsman, A. J. et al. (1995). Yeast retrotransposon particles as antigen delivery systems. Ann. N.Y. Acad. Sci. 754, 202–13.

Kochanek, S. et al. (1996). A new adenoviral vector: Replacement of all viral coding sequences with 28 kb of DNA independently expressing both full-length dystrophin and beta-galactosidase. Proc. Natl. Acad. Sci. USA 93, 5731–6.

Lieber, A. et al. (1996). Recombinant adenoviruses with large deletions generated by Cre-mediated excision exhibit different biological properties compared with first-generation vectors in vitro and in vivo. J. Virol. 70, 8944–60.

Lucher, L. (1995). Abortive adenovirus infection and host range determinants. In The Molecular Repertoire of Adenoviruses, W. Doerfler and P. Bohm, eds. (Berlin, Heidelberg, New York: Springer), pp. 119–152.

Mann, R. et al. (1983). Construction of a retrovirus packaging mutant and its use to produce helper-free defective retrovirus. Cell 33, 153–159.

Markowitz, D. et al. (1988). A safe packaging line for gene transfer: Separating viral genes on two different plasmids. J. Virol. 62, 120–124.

Miller, A. D., and Buttimore, C. (1986). Redesign of retrovirus packaging cell lines to avoid recombination leading to helper virus production. Mol. Cell. Biol. 6, 2895–2902.

Minakami, R. et al. (1992). Identification of an internal cis-element essential for the human L1 transcription and a nuclear factor(s) binding to the element. Nucl. Acids Res. 12, 3139–3145.

Mitani, K. et al. (1995A). Rescue, propagation, and partial purification of a helper virus-dependent adenovirus vector. Proc Natl Acad Sci USA 92, 3854–8.

Mitani, K. et al. (1995B). Gene targeting in mouse embryonic stem cells with an adenoviral vector. Somat. Cell. Mol. Genet. 21, 221–231.

Moran, J. V. et al. (1996). High frequency retrotransposition in cultured mammalian cells. Cell 87, 917–27.

Mulligan, R. (1993). The basic science of gene therapy. Science 260, 926–932.

Parks, R. J. et al. (1996). A helper-dependent adenovirus vector system: removal of helper virus by Cre-mediated excision of the viral packaging signal. Proc. Natl. Acad. Sci. USA 93, 13565–70.

Plasterk, R. H. (1999) Resident aliens: the Tc1/mariner superfamily of transposable elements. Trends Genet. 15, 326–32.

Plasterk, R. H. (1996) The Tc1/mariner transposon family. Curr. Top. Microbiol. Immunol. 204, 125–43.

Parks, R. J., and Graham, F. L. (1997). A helper-dependent system for adenovirus vector production helps define a lower limit for efficient DNA packaging. J. Virol. 71, 3293–8.

Roessler, B. J. et al. (1995). Inhibition of interleukin-1-induced effects in synoviocytes transduced with the human IL-1 receptor antagonist cDNA using an adenoviral vector. Hum. Gene Ther. 6, 307–316.

Sassaman, D. M. et al.(1997). Many human L1 elements are capable of retrotransposition [see comments]. Nat. Genet. 16, 37–43.

Savard, N. et al. (1997). Defective herpes simplex virus type 1 vectors harboring gag, pol, and env genes can be used to rescue defective retrovirus vectors. J. Virol. 71, 4111–7.

Scott, A. F. et al. (1987). Origin of the human L1 elements: proposed progenitor genes deduced from a consensus DNA sequence. Genomics 1, 113–125.

Singer, M. F. et al. (1993). LINE-1: a human transposable element. Gene 135, 183–188.

Soneoka, Y. et al. (1995). A transient three-plasmid expression system for the production of high titre retroviral vectors. Nucl. Acid Res. 23, 628–633.

Swergold, G. D. (1990). Identification, characterization, and cell specificity of a human LINE-1 promoter. Mol. Cell. Biol. 10, 6718–6729. Thrasher, A. J., de Alwis, M., Casimir, C. M., Kinnon, C., Page, K., Lebkowski, J., Segal, A. W., and Levinsky, R. J. (1995). Generation of recombinant adeno-associated virus (rAAV) from an adenoviral vector and functional reconstitution of the NADPH-oxidase. Gene Ther. 2, 481–5.

Torrent, C. et al. (1994). Analytical study of rat retrotransposon VL30 RNA dimerization in vitro and packaging in murine leukemia virus. J. Mol. Biol. 240, 434–44.

Varmus, H. (1988). Retroviruses. Science 240, 1427–1435.

Weiss, R. et al. (1984). RNA Tumor Viruses: Molecular Biology of Tumor Viruses (Cold Spring Harbor, N.Y.: Cold Spring Harbor Laboratory).

Xiong, Y., and Eickbush, T. H. (1990). Origin and evolution of retroelements based upon their reverse transcriptase sequences. EMBO J. 9, 3353–3362.

Yang, Y. et al. (1995). Cellular and humoral immune responses to viral antigens create barriers to lung-directed gene therapy with recombinant adenoviruses. J. Virol. 69, 2004–15.

Yoshida, Y. et al. (1997). VSV-G-pseudotyped retroviral packaging through adenovirus-mediated inducible gene expression. Biochem. Biophys. Res. Commun. 232, 379–82.

Yoshimoto, T. et al. (1993). Identification of amino acid residues critical for infection with ecotropic murine leukemia retrovirus. J. Virol. 67, 1310–1314.

What is claimed is:

1. A hybrid vector for genetic material delivery comprising a nucleic acid molecule comprising:
   (a) a helper-dependent adenoviral vector region comprising:
      (i) a first and a second adenoviral inverted terminal repeat, and
      (ii) an adenoviral packaging signal, wherein said adenoviral vector region lacks sequences encoding functional adenoviral genes necessary for replication or packaging; and
   (b) a non-LTR retrotransposon region comprising:
      (i) a first nucleic acid region encoding a non-LTR retrotransposon protein or proteins, and (ii) a promoter region comprising a 5' untranslated region of a non-LTR retrotransposon operably linked to said first nucleic acid region.

2. The hybrid vector of claim 1 wherein said retrotransposon region further comprises a second nucleic acid region encoding said genetic material for delivery operably linked to said first nucleic acid region, wherein said second nucleic acid region can be integrated into the host cell genome during the process of retrotransposition mediated by said retrotransposon proteins encoded by said first nucleic acid region.

3. The hybrid vector of claim 1 wherein said nucleic acid molecule is encapsidated by one or more helper adenovirus proteins for delivery as an adenovirus particle.

4. The hybrid vector of claim 1 wherein said first and second inverted terminal repeats comprise adenovirus serotype 2 or adenovirus serotype 5 sequences.

5. The hybrid vector of claim 1 wherein said adenoviral packaging signal is located adjacent to said first inverted terminal repeat.

6. The hybrid vector of claim 1 further comprising a retrotransposon sequence.

7. The hybrid vector of claim 1, wherein the adenoviral vector region lacks sequences encoding functional adenoviral structural genes.

8. The hybrid vector of claim 1, wherein the adenoviral vector region is a gutless adenoviral vector.

9. The hybrid vector of claim 1, wherein the non-LTR retrotransposon is from a L1 retrotransposon.

10. The hybrid vector of claim 2 wherein said second nucleic region comprises sequences to the 3' side of said first nucleic acid region.

11. The hybrid vector of claim 2 further comprising a polyadenylation site to the 3' side of said second nucleic acid region.

12. The hybrid vector of claim 6 wherein said retrotransposon sequence comprises a first open reading frame encoding a nucleic acid binding protein and a second open reading frame encoding an endonuclease and reverse transcriptase operably linked to said promoter.

13. The hybrid vector of claim 6 further comprising a viral promoter.

14. The hybrid vector of claim 13 wherein said promoter is an SV40 or a cytomegalovirus promoter.

* * * * *